United States Patent [19]
Garst et al.

[11] Patent Number: 5,468,778
[45] Date of Patent: Nov. 21, 1995

[54] METHOD OF LOWERING INTRAOCULAR PRESSURE BY ADMINISTERING A PHARMACEUTICAL COMPOSITION CONTAINING 7-(5-SUBSTITUTED CYCLOPENTYL) AND 7-(5-SUBSTITUTED-CYCLOPENTENYL) 5-HEPTENOIC ACIDS AND DERIVATIVES

[75] Inventors: Michael E. Garst, Newport Beach; Robert M. Burk, Laguna Beach; Ming F. Chan, San Diego; Michael B. Roof, Los Angeles, all of Calif.

[73] Assignee: Allergan, Inc., Irvine, Calif.

[21] Appl. No.: 950,855

[22] Filed: Sep. 24, 1992

[51] Int. Cl.$^6$ .......... A61K 31/19; A61K 31/215
[52] U.S. Cl. .......... 514/573; 514/530; 514/913
[58] Field of Search .......... 514/530, 573, 514/913

[56] References Cited

U.S. PATENT DOCUMENTS

| | | | |
|---|---|---|---|
| 3,903,143 | 9/1975 | Mueller | 260/514 |
| 4,033,992 | 7/1977 | Grudzinskas et al. | 260/456 |
| 4,599,353 | 7/1986 | Bito | 514/530 |
| 4,822,820 | 4/1989 | DeSantis et al. | 514/530 |
| 4,994,274 | 2/1991 | Chan et al. | 424/427 |
| 5,034,413 | 7/1991 | Chan et al. | 514/530 |

FOREIGN PATENT DOCUMENTS

| | | | |
|---|---|---|---|
| 0242580 | 10/1987 | European Pat. Off. | A61K 31/557 |
| 0364417 | 4/1990 | European Pat. Off. | A61K 31/557 |
| 1434620 | 5/1976 | United Kingdom | C07C 177/00 |
| WO9114428 | 10/1991 | WIPO | A61K 31/215 |

OTHER PUBLICATIONS

Bito, L. Z., *Arch. Ophthalmol*, 105, 1036 (1987).
Bito, L. Z., *Applied Pharmacology in the Medical Treatment of Glaucomas*, Drance, S. M. and Neufeld, A. H. eds., New York, Grune & Stratton, 1984 pp. 477–505.
Bito, L. Z., *Biological Protection with Prostaglandins*, Cohen, M. M., ed., Boca Raton Fla. CRC Press Inc., 1985, pp. 231–252.
M. S. Starr, *Exp. Eye Res.* 11, 170–177 (1971).
Nilsson et al., *Invest, Ophthalmol. Vis. Sci.* 28 (suppl), 284 (1987).
Siebold et al., *Prodrug* 5, 3 (1989).
Woodward, et al., Prostaglandin $F_{2\alpha}$ Effects on Intraocular Pressure Negatively Correlate with FP-Receptor Stimulation, *Investigative Ophthalmology & Visual Science*, vol. 30, No. 8, Aug. 1989.
Zajacz, et al., Effect on Human Eye of Prostaglandin and a Prostaglandin Analogue Used to Induce Abortion, *The Eye: Reproduction, Obstetrics and Gynecology*, 4, 316 (1976).

*Primary Examiner*—Zohreh Fay
*Attorney, Agent, or Firm*—Gabor L. Szekeres; Robert J. Baran; Martin A. Voet

[57] ABSTRACT

Intraocular pressure is lowered in the eye of a mammal by administration of a pharmaceutical composition containing as active ingredient a compound of the formula

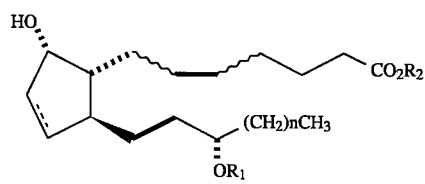

where the dotted line represents a bond or the absence of a bond, wavy lines connected to the olefinic bond represent cis or trans configuration about the olefinic bond; $R_1$ represents H, or CO-$R_3$ where $R_3$ is lower alkyl of 1 to 6 carbons, carbocyclic aryl or heterocyclic aryl; or carbocyclic aryl or heteroaryl substituted lower alkyl group; $R_2$ represents H or lower alkyl of 1 to 6 carbons, and n is an integer between 0 and 8.

23 Claims, No Drawings

METHOD OF LOWERING INTRAOCULAR PRESSURE BY ADMINISTERING A PHARMACEUTICAL COMPOSITION CONTAINING 7-(5-SUBSTITUTED CYCLOPENTYL) AND 7-(5-SUBSTITUTED-CYCLOPENTENYL) 5-HEPTENOIC ACIDS AND DERIVATIVES

FIELD OF THE INVENTION

The present invention is in the field of methods of lowering intraocular pressure in the eye of a mammal. More particularly the present invention is in the field of lowering intraocular pressure in the eye of a mammal by administering to the mammal a pharmaceutical composition which contains as its active ingredient one or more 7-(5-substituted cyclopentyl) or 7-(5-substituted-cyclopentenyl)-5-heptenoic acids or lower alkyl ester derivatives of said heptanoic acids.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing compete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical B-adrenoreceptor antagonists have traditionally been the drugs of choice for treating glaucoma.

Postaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, M. S. Starr, *Exp. Eye Res.* 11,170–177 (1971) Bito, L. Z. *Biological Protection with Prostaglandins* Cohen, M. M., ed., Boca Raton, Fla. CRC Press Inc., 1985, pp. 231–252; and Bito, L. Z., *Applied Pharmacology in the Medical Treatment of Glaucomas* Drance, S. M. and Neufeld, A. H. eds., N.Y., Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest, Ophthalmol. Vis. Sci.* 28 (suppl), 284 (1987) ].

The isopropyl ester of $PGF_{2\alpha}$ has been shown to have significantly greater hypotensive potency than the parent compounds, which was attributed to its more effective penetration through the cornea. In 1987 this compound was described as "the most potent ocular hypotensive agent ever reported." [See, for example, Bito, L. Z., *Arch. Ophthalmol,* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of postaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acylprostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15- 9,15-and 9,11-diesters of prostaglandins, for example 11,15-dipivaloyl $PGF_{2\alpha}$ are known to have ocular hypotensive activity. See the co-pending patent applications U.S. Ser. No. 385, 645 filed 25 Jul. 1990, now U.S. Pat. No. 4,494,274; 584,370 which is a continuation of U.S. Ser. No. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

SUMMARY OF THE INVENTION

It was found in accordance with the present invention that intraocular pressure in the eye of a mammal is lowered significantly when a pharmaceutical composition containing certain 7-(5-substituted cyclopentyl) and 7-(5-substituted cyclopentenyl)-5heptenoic acids or their derivatives, including their pharmaceutically acceptable salts, shown by Formula 1, is administered to the mammal.

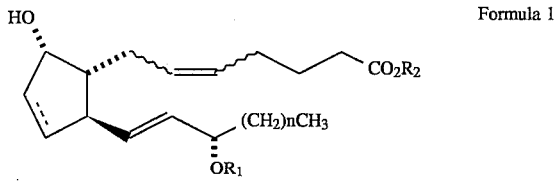

FORMULA 1

In Formula 1 the dotted line represents a bond, or the absence of a bond, and wavy lines attached to the double bond indicate cis or trans configuration about the double bond;

$R_1$ represents H, or $CO-R_3$ where $R_3$ is lower alkyl of 1 to 6 carbons, carbocyclic aryl or heterocyclic aryl; or carbocyclic aryl or heteroaryl substituted lower alkyl group;

$R_2$ represents H or lower alkyl of 1 to 6 carbons, and n is an integer between 0 and 8.

Thus, the present invention relates to pharmaceutical compositions adapted for lowering intraocular pressure in the eye of a mammal, said compositions containing as active ingredient one or more compounds of Formula 1, and to methods of administering said compositions to a mammal for the purpose of lowering intraocular pressure.

DETAILED DESCRIPTION OF THE INVENTION

GENERAL EMBODIMENTS

The present invention relates to the use of compounds of Formula 1 in pharmaceutical compositions and methods for the purpose of lowering intraocular pressure in the eye of a mammal.

Definitions

In Formula 1 as well as in all other chemical formulas in the present application for United States letters patent, bonds shown with hashed lines indicate a bond below the plane of the paper, thus signifying α configuration; bonds shown as a solid triangle indicate a bond above the plane of the paper, thus signifying β configuration; a dashed or dotted line represents a single bond or absence of a bond, and wavy lines attached to a double bond indicate that the configuration of substituents about the double bond can be cis or trans. Trans (E) configuration of substituents about a double bond is indicated by bonds pointing in opposite directions about a double bond, whereas cis (Z) configuration of substituents about a double bond is indicated by bonds pointing in the same direction about a double bond.

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups.

The term "ester" as used here refers to and covers any compound falling within the definition of that term classically used in organic chemistry. Where the ester is derived from a carboxylic acid corresponding to Formula 1, the term covers the products derived from the treatment of this function with alcohols, preferably with aliphatic alcohols having 1–6 carbons. Where the ester is derived from alcohols corresponding to Formula 1, the term covers compounds of the formula $-CH-OOCR_3$ where $R_3$ is lower alkyl, carbocyclic aryl, heteroaryl, or carbocyclic aryl or heteroaryl substituted lower alkyl group.

A pharmaceutically acceptable salt may be prepared for any compound used in the method of treatment of this invention, if the compound has a functionality capable of forming such salt, for example an acid functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalention. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethanine and similar molecules.

The compounds utilized in accordance with the method of treatment of the present invention, contain at least one double bond and therefore have trans and cis (E and Z) isomers. In addition, the compounds used in the method of treatment of the present invention contain one or more chiral centers and therefore exist in enantiomeric and diastereomeric forms. Unless the structural formula or the language of this application specifically designate a particular cis or trans isomer or a particular configuration of a chiral center, the scope of the present invention is intended to cover all such isomers per se, as well as mixtures of cis and trans isomers, mixtures of diastereomers and racemic mixtures of enantiomers (optical isomers) as well.

For the sake of ease of description, the side chain in Formula 1 which contains the heptanoic acid residue is sometimes referred to in the application as the "heptanoic acid side chain", and the other side chain attached to the cyclopentane or cyclopentene ring in accordance with Formula 1 is sometimes called as the "3-α- hydroxy side chain", or as the "3-α-hydroxyoctenyl side chain".

General Description of Preferred Compounds Used in the Method of the Invention Referring now to the structure shown in Formula 1, preferred compounds used in the method of treatment of the invention are those where $R_1$ is hydrogen or $CO-R_3$, where $R_3$ is alkyl of 1 to 3 carbons.

With reference to $R_2$ in Formula 1, the preferred compounds used in accordance with the invention are those where $R_2$ is hydrogen or a pharmaceutically acceptable cation (the compound is a carboxylic acid a pharmaceutically acceptable salt thereof), or where $R_2$ is lower alkyl of 1 to 3 carbons.

With respect to the double bond in the heptenoic acid side chain of Formula 1, compounds are preferred in accordance with the present invention where that double bond is in the cis (Z) configuration. The double bond in the 3-α-hydroxy side chain is always in the trans configuration in the compounds used in the method of the present invention.

With regard to n in the 3-α-hydroxyl side chain of the compounds of Formula 1, n is preferably 4.

The most preferred compounds used in the method of the present invention are indicated by their structural formula, as compounds 1–2, respectively.

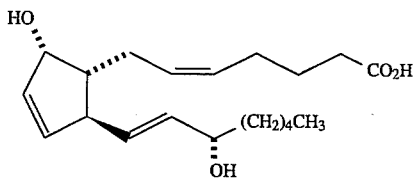

Compound 1

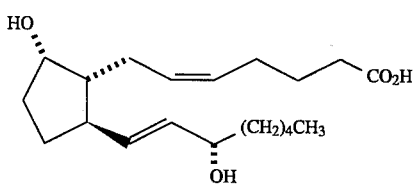

Compound 2

Methods of Administration, Formulations

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0,001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisol and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop is about 20–35 μl.

Biological Activity

The ability of a pharmaceutical composition which contains a compound of Formula 1 to lower intraocular pressure in the eye of a mammal, can be demonstrated by an assay performed on the eyes on New Zealand Dutch belted crossbred rabbits. The assay is performed as follows.

New Zealand, albino/Dutch-belted cross-bred rabbits of either sex and weighing 1.5–2.5 kg were used, which had not previously received topical drugs of any kind. Intraocular pressure was measured with a pneumatonometer (Digilab) calibrated against the eyes of anesthetized rabbits by closed stopcock manometry. The correlation coefficient over a 10–30 mm Hg range was 0.98. The animals were acclimated to pneumatonometry by taking unrecorded measurements before experimental determinations of intraocular pressure. Corneal anesthesia for tonometry was provided by topical application of one drop of proparacaine (Allergan, Irvine, Calif.).

The data obtained by measuring intraocular pressure in this assay 1,2,4,4 and 6 hours after topical administration of 20 microliters of 0.01% and 0.1% isotonic solutions of Compound 1 and of Compound 2 in accordance with the present invention are illustrated below in Table 1 (Compound 1) and Table 2 (Compound 2), respectively

TABLE 1

| Compound # | (Dose %) | 1 hr | 2 hr | 3 hr | 4 hr | 6 hr |
|---|---|---|---|---|---|---|
| EFFECT ON RABBIT INTRAOCULAR PRESSURE (mmHg); CHANGES AT PREDETERMINED TIMES (HR) AFTER DRUG ADMINISTRATION | | | | | | |
| Compound 1 | 0.1% | −0.60 | −2.86 | −1.34 | −1.94 | −1.10 |
| % ANIMALS EXHIBITING OCULAR SURFACE HYPEREMIA AT PREDETERMINED TIMES (HR) AFTER DRUG ADMINISTRATION | | | | | | |
| Compound 1 | 0.1% | 100 | 50 | 50 | 12.5 | 12.5 |

TABLE 2

| Compound # | (Dose %) | 1 hr | 2 hr | 3 hr | 4 hr | 6 hr |
|---|---|---|---|---|---|---|
| EFFECT ON RABBIT INTRAOCULAR PRESSURE (mmHg) CHANGES AT PREDETERMINED TIMES (HR) AFTER DRUG ADMINISTRATION | | | | | | |
| Compound 2 | 0.01% | −2.7 | −1.2 | −0.7 | −0.2 | −1.4 |
| Compound 2 | 0.1% | −3.5 | −6.8 | −8.4 | −7.6 | −3.3 |
| % ANIMALS EXHIBITING OCULAR SURFACE HYPEREMIA AT PREDETERMINED TIMES (HR) AFTER DRUG ADMINISTRATION | | | | | | |
| Compound 2 | 0.01% | 16.5 | 16.5 | 16.5 | 0 | 0 |
| Compound 2 | 0.1% | 100 | 100 | 100 | 66 | 50 |

The tables also show the percentage of rabbits which exhibited hyperemia (redness in the eye) 1,2,3,4 and 6 hours after topical administration of the active compound. As is well known hyperemia is an undesirable side effect, and the data illustrate that administration of the compounds in accordance with the method of the invention causes this side effect only to a moderate to minimal degree.

An in vitro assay by which the beneficial IOP lowering activity of the compounds utilized in the method of the present invention can be demonstrated is the intracellular $Ca^{2+}$ concentration assay, which is described as follows:

Measurement of intracellular $[Ca^{2+}]$ is achieved by incorporating the $Ca^{2+}$ sensitive fluorescent probe Fura-2AM into Swiss 3T3 cells in suspension as described by Yamaguchi, D. T. et al., J. Biol. Chem. 263: 10745–10753. Fluorescence is measured in a Perkin-Elmer LS-5 spectrophotometer at excitation and emission wavelengths of 340 and 492 nM, respectively. Each experimental determination employs $10^6$ cells suspended in Schmuells buffer. For studies in $Ca^{2+}$-free Schmuells buffer, each cuvette also contains −0.4 mN EGTA. Calibration of the Fura 2 signal is as previously described for Quin 2 (Tsien, R. Y. et al., (1982), J. Cell. Biol. 94: 325–334) and Fura 2 (Yamaguchi, supra). Briefly the cells are lysed with digitonin (10 μl×100 mg/ml) in DMSO). EGTA (100 mM) and sufficient 10N NaOH to adjust the pH to 8.5 were then successively added to obtain minimum fluorescence.

As is known in the art, and is described in an article titled "$Ca^{2+}$ transients evoked by prostanoids in Swiss 3T3 cells . . . " by D. F. Woodward et al., Advances in Prostaglandin, Thromboxane and Leukotriene Research, Vol. 21, B. Samuelson et al., editors, Raven Press Ltd. N.Y., activity in this assay indicates action as an agonist of the biological FP receptor, which in turn is believed to be a prime mediator for facilitating outflow of aqueous humor from the mammalian eye, thereby lowering intraocular pressure.

Synthetic Procedures For Obtaining Compounds Used In The Method of the Invention.

The compounds used in the novel methods of treatment of the invention can be made by a number of different synthetic chemical pathways. To illustrate the invention, the following detailed description is provided, with primary emphasis on the synthesis of preferred Compounds 1 and 2. The synthetic chemist will readily appreciate that the conditions set out here are specific embodiments which can be generalized to obtain any and all compounds described in the present specification.

Referring now to Reaction Scheme 1, the compound 7α-[2-oxo-5β-(3α-hydroxyl-1-trans-octenyl)-3-cyclopentenyl] -5-cis-heptenoic acid (Compound 10) serves as a starting material. Compound 10 is also called prostaglandin $A_2$, and is available commercially (Cayman Chemical Co., Ann Arbor, Mich.). In order to obtain Compounds 1 and 2, through steps of reduction, the carboxylic acid group of Compound 10 is protected by reaction with O-(2-trimethylsilyl)ethyl-N,N'-diisopropylisourea, to yield the intermediate compound (2-trimethylsilyl)ethyl 7α-[2-oxo-5β-(3α-hydroxyl-1-transoctenyl) -3-cyclopentenyl]-5-cis-heptenoate (Compound 11).

Reaction Scheme 1
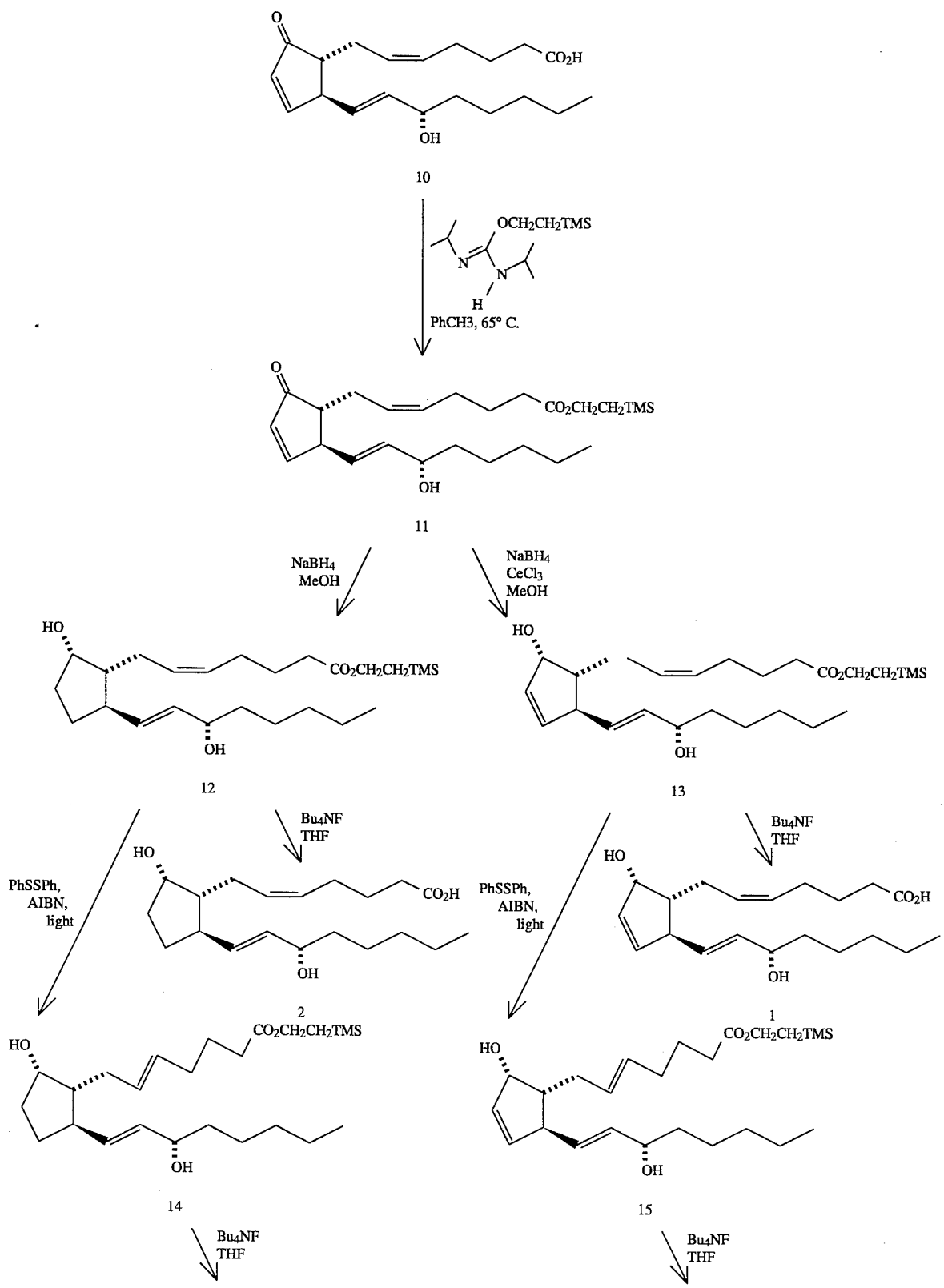

-continued
Reaction Scheme 1

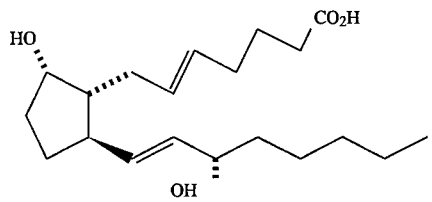

16

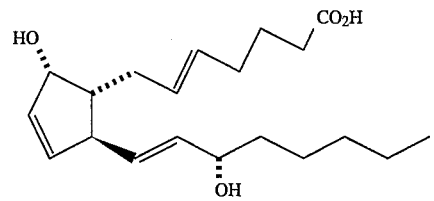

17

The oxo function and the double bond of the cyclopentene ring of Compound 11 are reduced with sodium tetrahydridoborate to provide a mixture of α and β-cyclopentanol derivatives, which are separated by chromatography. The cyclopentanol of α configuration (Compound 12) is thereafter deprotected on the carboxylic acid function by treatment with tetrabutylammonium fluoride to yield Compound 2.

The oxo function of the cyclopentene ring of Compound 11 is selectively reduced (without affecting the double bond in the ring) by treatment with sodium tetrahydridoborate in the presence of cerium trichloride, to yield a mixture of α and β-cyclopentenols, which are separated by chromatography. The α-cyclopenten-ol (Compound 13) is deprotected (on the carboxylic acid group) to yield Compound 1).

In order to obtain the isomers of Compounds 1 and 2 where the olefhinic bond of the 5-heptenoic acid moiety is in the trans configuration, intermediate Compound 12 or intermediate Compound 13 is isomerized by irradation with U.V. light (for approximately 4 hours) in toluene as a solvent, in the presence of phenyldisulfide and 2,2'-azobisisobutyronitrile (AIBN). The resulting intermediates, Compounds 14 and 15 are deprotected by removal of the (2-trimethylsilyl)ethyl group from the carboxylic acid moiety, to yield Compounds 16 and 17, which are the trans isomers (in the heptenoic acid chain) of Compounds 2 and 1, respectively.

An alternative procedure for obtaining Compound 2 is described with reference to Reaction Scheme 2 from commercially available (Cayman Chemical) 7-[3α,5α-dihydroxyl-2β-(3α-hydroxyl-1-trans-octenyl)-1α-cyclopentyl]-5-cis-heptenoic acid (Compound 20). The conditions of this sequence of reactions are indicated in the reaction scheme itself, and are further elaborated as follows. Compound 20 is reacted with diazomethane to yield the methyl ester (Compound 21) of the heptenoic acid moiety.

Reaction Scheme 2

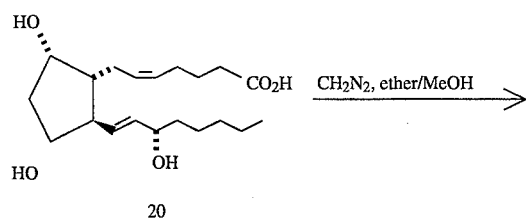

20

-continued
Reaction Scheme 2

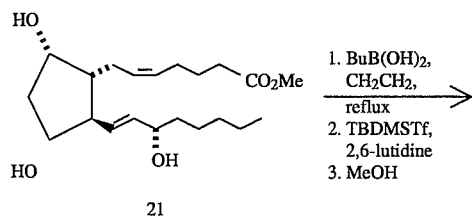

21

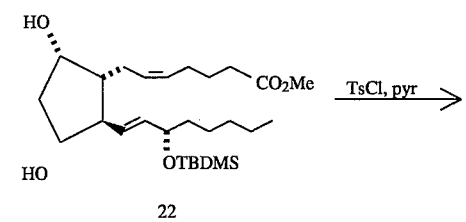

22

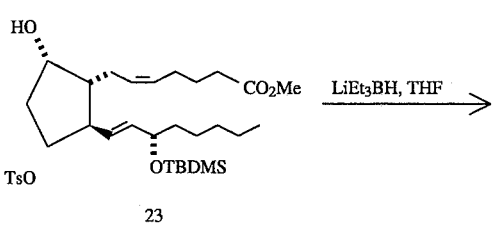

23

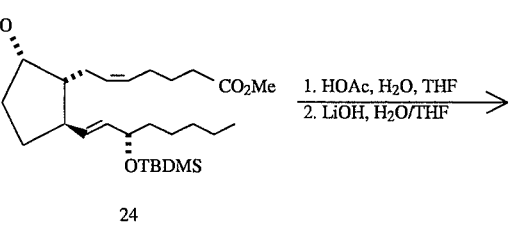

24

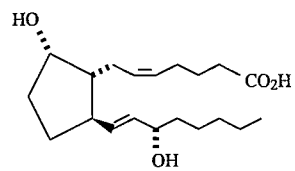

2

The 1,3-diol function of Compound 21 is then temporarily blocked by treatment with butylboronic acid (BuB(OH)$_2$), and a t-butyldimethylsilyl protecting group is introduced to the 3-α-hydroxy group in the 3-α-hydroxy octenyl side chain. This is followed by deprotection of the 1,3-diol function by methanol, to yield Compound 22. Compound 22 is p-toluenesulphonylated (tosylated) on the 4-α-hydroxyl group of the cyclopentane ring to yield Compound 23. Compound 23 is then reduced with lithium triethylborohydride (also known as Super-Hydride, which is a registered trademark of Aldrich Chemical Co.) to yield Compound 24 wherein one of the hydroxyl groups of the cyclopentane ring has been replaced with hydrogen. Thereafter, the t-butyldimethylsilyl blocking group of Compound 24 is removed by treatment with aqueous acetic acid, and the methyl ester of the heptenoic acid side chain is saponified with aqueous base (LiOH), to yield Compound 2.

Esters of the heptenoic acid moiety can be made in accordance with synthetic methods well known in the art. In this regard it is noted that carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide in dimethylaminopyridine. The ester is recovered and purified by conventional means.

The 3α-hydroxyl group of the 3α-hydroxyl side chain can be esterified by standard methods of esterification to give compounds of Formula 1 where $R_1$ represents an acyl (CO-$R_3$) group. The standards methods of esterification (such as DMAP catalyzed reaction with a carboxylic acid anhydride ($R_3$-CO)$_2$O, reaction with an acid chloride $R_3$-COCl, or reaction with an acid $R_3$-COOH in dimethylaminopyridine in the presence of dicyclohexylcarbodiimide) preferentially esterify the 3α-hydroxyl group over the hydroxyl group attached to the cyclopentane or cyclopentene ring.

Compounds used in the method of the present invention where, with reference to Formula 1, n is other than 4, can be obtained in accordance with Reaction Scheme 3.

32. The "enone" (Compound 32) is reduced by treatment with sodium borohydride in the presence of cerium trichloride to provide Compound 33. The 2-(trimethylsilyl) ethyl protecting group is then removed from the heptenoic acid side chain to provide the compounds which are used in the method of treatment of the present invention.

Specific Examples (2-Trimethylsilyl) ethyl 7α-[2-oxo-5β-(3α-hydroxy-1-transoctenyl) -3-cyclopentenyl]-5-cis-heptenoate (Compound 11)

A solution of 7α-[2-oxo-5β- (3α-hydroxy-1-transoctenyl) -3-cyclopentenyl)-5-cis heptenoic acid (Compound 10, 500 mg, 1.49 mmol) and O-(2-trimethylsilyl) ethyl-N,N'-diisopropylisourea (547 mg, 2.24 mmol) in toluene (4.5 mL) was heated to 65° C. for 16 hours. The reaction was allowed to cool to room temperature and concentrated in vacuo. Purification of the residue by flash column chromatography (silica gel, 2:1 hexane/EtOAc) afforded 508 mg (79%) of the title compound as a clear, colorless oil: $^1$H NMR (250 MHz, CDCl$_3$) δ7.50 (dd, J=2.0, 4.8 Hz, 1H), 6.19 (dd, J= 2.0, 4.8 Hz, 1H), 5.62–5.35 (m, 2H), 4.16 (t, J=7.0 Hz, 2H), 4.12–4.08 (m, 1H), 3.26–3.23 (m, 1H), 3.04 (d, J = 4.2 Hz, 1H), 2.75–2.08 (m, 7H), 1.74–1.29 (m, 10H), 0.98 (t, J=7.0 Hz, 2H), 0.90 (t, J = 5.8 Hz, 3H), 0.05 (s, 9H).

(2-Trimethylsilyl) ethyl 7α- [2α-hydroxy-5β -(3α-hydroxy-1-trans-octenyl) cyclopentyl]-5-cis-heptenoate(Compound 12)

Sodium tetrahydridoborate ( 9.1 mg, 0.241 mmol) was added to a solution of (2-trimethylsilyl)ethyl 7α- [2-oxo-5β-(3α-hydroxy-1-trans-octenyl)-3-cyclopentenyl] -5-cis-heptenoate (Compound 11, 105 mg, 0.241 mmol) in methanol (0.6 mL) at 23° C. The reaction was stirred for 2 hours and quenched with saturated aqueous ammonium chloride (2.0 mL). The resultant mixture was extracted with CH$_2$Cl$_2$ (2×) and the combined organics were dried (Na$_2$SO$_4$), Reaction Scheme 3

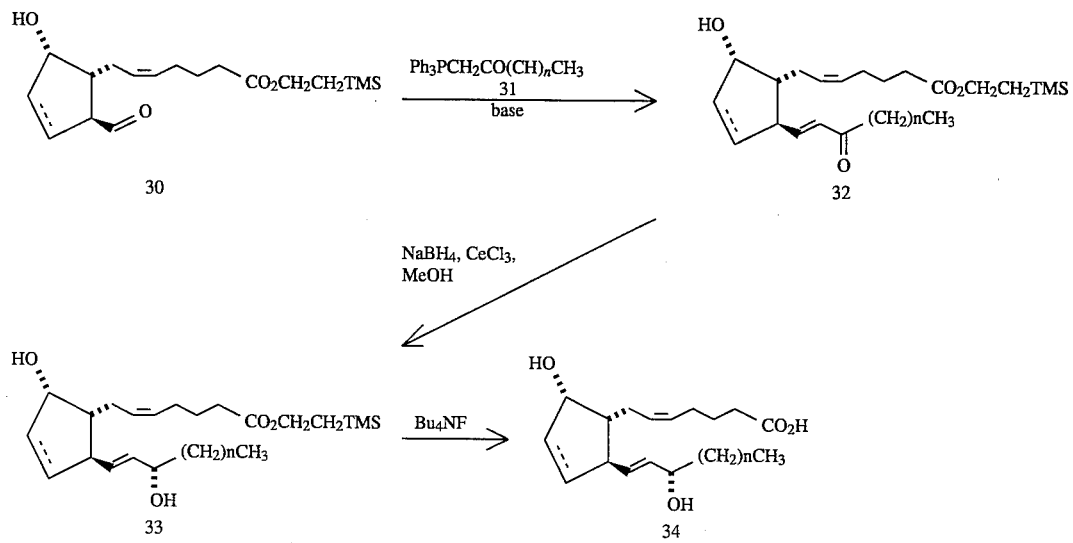

In accordance with this scheme, the starting material Compound 30 is an appropriately protected aldehyde which is reacted in a Wittig reaction with the phosphonium ylide reagent of Compound 31 to yield the "enone", Compound filtered and the filtrate concentrated in vacuo. Purification of the residue by flash column chromatography (silica gel, 3:1 hexane/EtOAc) afforded 20.7 mg (20%) of the title compound, α-alcohol and 40.4 mg (38%) of the corresponding β-alcohol. $^1$H NMR (250 MHz, CDCl$_3$) for α-alcohol 3: δ5.49–5.35 (m, 2H), 4.25–4.20 (m, 1H), 4.16 (t, J=7.0 Hz, 2H), 4.10–4.00 (m, 1H), 2.41–1.90 (m, 8H), 1.70–1.28 (m, 16H), 0.98 (t, J=7.0 Hz, 2H), 0.87 (t, J=5.8 Hz, 3H), 0.04 (s, 9H).

(2-Trimethylsilyl)ethyl 7α-[2α-hydroxy-5β-(3α-hydroxy-1-trans -octenyl)-3-cyclopentenyl]-5-cis-heptenoate (Compound 13)

The solution of the (2-trimethylsilyl)ethyl 7α-[2-oxo -5β-(3α-hydroxy-1-trans-octenyl)-3-cyclopentenyl]-5 -cis-heptenoate (Compound 11, 110 mg, 0,253 mmol) in methanolic cerium trichloride heptahydrate (0.63 mL of a 0.4M solution in MeOH, 0.253 mmol) was treated with sodium tetrahydridoborate (9.6 mg, 0.253 mmol) at 23° C. The reaction was stirred for 2 hours and quenched with saturated aqueous ammonium chloride (2.0 mL). The resultant mixture was extracted with CH$_2$Cl$_2$ (2×) and the combined organics were dried (Na$_2$SO$_4$), filtered and the filtrate concentrated in vacuo. Purification of the residue by flash column chromatography (silica gel, 4:1 hexane/EtOAc) afforded 17.9 mg (16%) of the title compound, α-alcohol and 28.4 mg (26%) of the corresponding β-alcohol. $^1$H NMR (250 MHz, CDCl$_3$) for α-alcohol 4: δ5.96–5.88 (m, 2H), 5.53–5.35 (m, 4H), 4.67–4.65 (m, 1H), 4.15 (t, J=7.0 Hz, 2H), 4.08–4.02 (m, 1H), 3.05–3.02 (m, 1H), 2.32–2.09 (m, 7H), 1.76–1.23 (m, 12H), 0.98 (t, J=7.0 Hz, 2H), 0.88 (t, J=5.8 Hz, 3H), 0.04 ( s, 9H).

7α- [2α-hydroxy-5β- (3α-hydroxy-1-trans-octenyl) -cyclopentyl ]-5-cis-heptenoic acid (Compound 2).

A solution of (2-trimethylsilyl)ethyl 7α-[2α -hydroxy-5β-(3α-hydroxy-1-trans-octenyl)cyclopentyl]-5 -cis-heptenoate (Compound 12) and tetrabutylammonium fluoride (62 µL of a 1.0M solution in THF, 0.062 mmol) in THF (0.5 mL) was stirred for 16 hours at 23° C. The reaction was diluted with EtOAc and washed with H$_2$O. The organic portion was dried (MgSO$_4$), filtered and concentrated in vacuo. Purification of the residue by flash column chromatography (silica gel, 9:1 CH$_2$Cl$_2$/MeOH) afforded 8.2 mg (60%) of the title compound. $^1$H NMR (250 MHz, CDCl$_3$): δ12.0 (brs, 1H), 5.57–5.33 (m, 4H), 4.25–4.21 (m, 1H), 4.16 (4.09 (m, 1H), 3.20 (br s, 2H), 2.35–2.19 (m, 3H), 2.17– 1.90 (m, 6H), 1.72–1.20 (m, 13H), 0.86 (t, J=5.8 Hz, 3H).

7α-[2α-hydroxy-5β-(3α-hydroxy-1-trans-octenyl)-3-cyclopentenyl] -5-cis-heptenoic acid (Compound 1)

Similarly to the deprotection of Compound 12, (2-trimethylsilyl) ethyl 7α-[2α-hydroxy-5β-(3α-hydroxy-1 -trans-octenyl)-3-cyclopentenyl]-5-cis-heptenoate (Compound 13) was treated with tetrabutylammonium fluoride to yield 12.7 mg (82%) of the title compound. $^1$H NMR δ11.5 (br s, 1H), 5.98–5.85 (m, 2H), 5.65– 5.33 (m, 4H), 4.68–4.66 (m, 1H), 4.20–4.16 (m, 1H), 3.70 (br s, 2H), 3.10–3.03 (m, 1H), 2.37–2.06 (m, 7H), 1.76–1.25 (m, 10H), 0.88 (t, J=5.0 Hz, 3H).

What is claimed is:

1. A method for lowering intraocular pressure in the eye of a mammal, which comprises administering to the mammal a pharmaceutical composition containing a pharmaceutically acceptable excipient and an effective amount of a compound having the formula

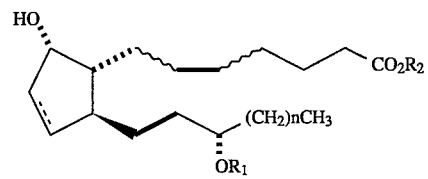

wherein the dotted line represents a bond or the absence of a bond, wavy lines attached to a double bond indicate cis or trans configuration about the double bond;

$R_1$ represents H, or CO-$R_3$ where $R_3$ is lower alkyl of 1 to 6 carbons, or carbocyclic aryl.

$R_2$ represents H or lower alkyl of 1 to 6 carbons, and n is an integer between 0 and 8.

2. The method of claim 1 wherein the bonds indicated by wavy lines define cis configuration about the olefinic bond.

3. The method of claim 1 wherein the bonds indicated by wavy lines define trans configuration about the olefinic bond.

4. The method of claim 1 wherein $R_1$ is hydrogen.

5. The method of claim 1 wherein $R_2$ is H.

6. The method of claim 1 wherein n is 4.

7. A method for lowering intraocular pressure in the eye of a mammal, which comprises administering to the mammal a pharmaceutical composition containing a pharmaceutically acceptable excipient and an effective amount of a compound having the formula:

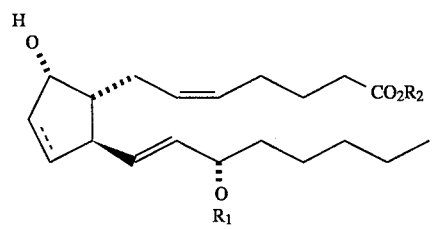

wherein the dotted line within the 5-membered alicyclic ring represents a bond or the absence of a bond;

$R_1$ is H or CO-$R_3$ where $R_3$ is lower alkyl of 1 to 6 carbons or phenyl, or phenyl substituted with lower alkyl, lower alkoxy or halogen groups, and $R_2$ is H or lower alkyl of 1 to 6 carbons.

8. The method of claim 7 wherein the dotted line represents a bond.

9. The method of claim 8 wherein $R_1$ is H.

10. The method of claim 8 wherein $R_2$ is H.

11. The method of claim 8 wherein $R_1$ and $R_2$ are hydrogen.

12. The method of claim 7 wherein the dotted line represents absence of a bond.

13. The method of claim 12 wherein $R_1$ is H.

14. The method of claim 12 wherein $R_2$ is H.

15. The method of claim 12 wherein $R_1$ and $R_2$ are hydrogen.

16. A method for lowering intraocular pressure, in the eye of a mammal, which comprises topically administering to the mammal a pharmaceutical composition adapted for topical administration, the composition containing a pharmaceutically acceptable excipient and an effective amount of a compound which has the formula

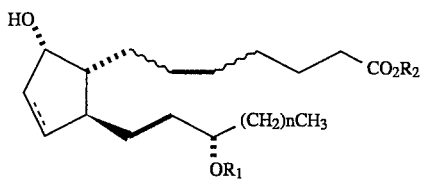

wherein the dotted line within the ring represents a bond or the absence of a bond, the wavy lines connected to the olefinic bond represent bonds which can be in cis or trans configuration about the olefinic bond;

$R_1$ represents H or CO-$R_3$ where $R_3$ is lower alkyl of 1 to 6 carbons, or carbocyclic aryl.

$R_2$ represents H or lower alkyl of 1 to 6 carbons, and n is an integer between 0 and 8.

17. The method of claim 16 wherein the pharmaceutical composition is an ophtalmic solution.

18. The method of claim 17 wherein n is 4.

19. The method of claim 18 wherein the wavy lines connected to the olefinic bond represent cis configuration about the bond.

20. The method of claim 19 wherein the dashed line in the ring represents absence of a bond.

21. The method of claim 20 wherein $R_1$ and $R_2$ are H.

22. The method of claim 19 wherein the dashed line in the ring represents a bond.

23. The method of claim 22 wherein $R_1$ and $R_2$ are H.

* * * * *

UNITED STATES PATENT AND TRADEMARK OFFICE
CERTIFICATE OF CORRECTION

PATENT NO. : 5,468,778
DATED : November 21, 1995
INVENTOR(S) : Garst et al.

It is certified that error appears in the above-indentified patent and that said Letters Patent is hereby corrected as shown below:

Column 2, line 55, "filed 25 July 1990" should be --filed 27 July, 1990--;

Column 2, line 58, "386,834" should be --385,834--;

Column 3, line 1, "5heptenoic" should be -- 5-heptenoic --;

Column 5, line 33, "0,001" should be --0.001--.

Column 8, line 9, after "DMSO" please delete ")";

Column 15, line 45, "4.16 (4.09" should be --4.16-4.09 --.

Signed and Sealed this

Nineteenth Day of November, 1996

Attest:

BRUCE LEHMAN

Attesting Officer

Commissioner of Patents and Trademarks